United States Patent [19]
Price et al.

[11] Patent Number: 5,869,287
[45] Date of Patent: Feb. 9, 1999

[54] METHOD OF PRODUCING PARTICLES CONTAINING NUCLEIC ACID SEQUENCES IN YEAST

[75] Inventors: B. Duane Price; Roland R. Rueckert; Michael A. Krol; Paul G. Ahlquist, all of Madison, Wis.

[73] Assignee: Wisconsin Alumni Research Foundation, Madison, Wis.

[21] Appl. No.: 682,827

[22] Filed: Jul. 12, 1996

[51] Int. Cl.⁶ .................................................... C12P 21/06
[52] U.S. Cl. .................... 435/69.1; 435/91.1; 435/91.33; 435/239; 435/254.21
[58] Field of Search ................................ 435/235, 172.1, 435/172.3, 69.1, 320.1, 91.1, 91.33, 239, 254.21; 536/24.1, 23.1, 23.72, 24

[56] References Cited

U.S. PATENT DOCUMENTS

| | | | |
|---|---|---|---|
| 4,879,236 | 11/1989 | Smith et al. | 435/320.1 |
| 4,885,248 | 12/1989 | Ahlquist | 435/252.33 |
| 5,466,788 | 11/1995 | Ahlquist et al. | 536/24.1 |
| 5,500,360 | 3/1996 | Ahlquist et al. | 435/172.3 |
| 5,602,242 | 2/1997 | Ahlquist et al. | 536/23.72 |

FOREIGN PATENT DOCUMENTS 0 194 809 B1  3/1991  European Pat. Off. .

OTHER PUBLICATIONS

M. Janda and P. Ahlquist, "RNA–Dependent Replication, Transcription, and Persistence of Brome Mosaic Virus RNA Replicons in S. Cerevisiae," *Cell* 72:961–970, 1993.

B.H. Selling, et al., "Genomic RNA of an insect virus directs synthesis of infectious virions in plants," *Proc. Natl. Acad. Sci. USA* 87:434–438, 1990.

L.A. Ball, et al., "Replication of Nodamura Virus after Transfections of Viral RNA into Mammalian Cells in Culture," *Journal of Virology* 66(4):2326–2334, 1992.

L.A. Ball, "Replication of the genomic RNA of a positive–strand RNA animal virus from negative–sense transcripts," *Proc. Natl. Acad. Sci. USA* 91(26):12443–12447, 1994.

R.H. Coutts, et al., "Infection of Protoplasts from Yeast with Tobacco Mosaic Virus", *Nature* 240(5382):466–467, 1972.

P. Coward and A. Dasgupta, "Yeast Cells Are Incapable of Translating RNAs Containing the Poliovirus 5' Untranslated Region: Evidence for a Translational Inhibitor," *Journal of Virology* 66(1):286–295, 1992.

S. Das, et al., "A Small Yeast RNA Selectively Inhibits Internal Initiation of Translation Programmed by Poliovirus RNA: Specific Interaction with Cellular Proteins That Bind to the Viral 5'–Untranslated Region," *Journal of Virology* 68(11):7200–7211, 1994.

E.A. Emini, et al., "Production and immunological analysis of recombinant hepatitis B vaccine, " *Journal of Infection* 13(Suppl. A):3–9, 1986.

P.V. Hamsa and B.B. Chattoo, "Cloning and growth–regulated expression of the gene encoding the hepatitis B virus middle surface antigen in *Yarrowia lipolytica*," *Gene* 143(2):165–170, 1994.

K.J. Hofmann, et al., "Sequence Determination of Human Papillomavirus Type 6a and Assembly of Virus–like Particles in *Saccharomyces cerevisiae*," *Virology* 209(2):506–518, 1995.

K.J. Hofmann, et al., "Sequence Conservation within the major capsid protein of human papillomavirus (HPV) type 18 and formation of HPV–18 virus–like particles in *Saccharomyces cerevisiae*," *Journal of General Virology* 77(Pt 3):465–468, 1996.

M.N. Jagadish, et al., "Expression of potyvirus coat protein in *Escherichia coli* and yeast and its assembly into virus––like particles," *Journal of General Virology* 72(pt 7):1543–1550, 1991.

Z.A. Janowicz, et al., "Simultaneous Expression of the S and L Surface Antigens of Hepatitis B, and Formation of Mixed Particles in the Methylotrophic Yeast, *Hansenula polymorpha*," *Yeast* 7(5):431–443, 1991.

J.P.M. Jore, et al., "Formation of Poliomyelitis Subrival Particles in the Yeast *Saccharomyces cerevisiae*,"*Yeast* 10(7):907–922, 1994.

R.A.Kramer, et al., "HTLV–III gag Protein is Processed in Yeast Cells by the Virus *pol–protease*," *Science* 231(4745):1580–1584, 1986.

P. Lhoas, "Mating Pairs of *Saccharomyces cerevisiae* infected with Double Stranded RNA Viruses from *Aspergillus niger*," *Nature –New Biology* 236(64):86–7, 1972.

R. Quadt, et al., "Formation of brone mosaic virus RNA–dependent RNA polymerase in yeast requires coexpression of viral proteins and viral RNA," *Proc. Natl. Acad. Sci. USA* 92(11):4892–4896, 1995.

T. Sasagawa, et al., "Synthesis and Assembly of Virus–like Particles of Human Papillomaviruses Type 6 and Type 16 in Fission Yeast *Schizosaccharomyces pombe*," *Virology* 206(1):126–135, 1995.

M.J. Schmitt and F. Neuhausen, "Killer Toxin–Secreting Double–Stranded RNA Mycoviruses in the Yeasts *Hanseniaspora uvarum* and *Zygosaccharomyces bailii*," *Journal of Virology* 68(3):1765–11772, 1994.

(List continued on next page.)

*Primary Examiner*—James Ketter
*Assistant Examiner*—Irem Yucel
*Attorney, Agent, or Firm*—Quarles & Brady

[57] ABSTRACT

A method of synthesizing particles containing nucleic acid sequences is disclosed. This method comprises the steps of introducing a non-endogenous packageable nucleic acid sequence and a sequence encoding a suitable non-endogenous capsid protein into yeast cells and inducing particle assembly, wherein at least one nucleic acid is encapsidated. Preferably, the particle is an infectious virion and the method additionally comprises the step of inducing viral nucleic acid replication before particle assembly. A method of replicating an animal or Nodaviridae virus nucleic acid sequences in yeast is also disclosed.

8 Claims, 5 Drawing Sheets

OTHER PUBLICATIONS

S.H. Shen, et al., "Synthesis and secretion of hepatitis B middle surface antigen by the methylotrophic yeast *Hansenula polymorpha* ," *Gene* 84(2):303–309, 1989.

K. Shiosaki, et al., "Production of hepatitis B virion–like particles in yeast ," *Gene* 106(2):143–149, 1991.

K. Yoshioka, et al., "Production of a unique multi–lamella structure in the nuclei of yeast expressing *Drosophila copia gag* precursor," *FEBs Letters* 302(1):5–7, 1992.

W. Zhong, "Flock House Virus, a Small Insect Ribovirus: Replication and Encapsidation of RNA2," *Madison: University of Wisconsin –Madison* pp. 119–138, 1993.

B.Price, et al., "Complete replication of an animal virus and maintenance of expression vectors derived from it in *Saccharomyces cerevisiae*," 93:9465–9470, 1996.

A. Schneemann, et al., "Use of Recombinant Baculoviruses in Synthesis of Morphologically Distinct Viruslike Particles of flock House Virus, a Nodavirus," 67(5):2756–2763, 1993.

METHOD OF PRODUCING PARTICLES CONTAINING NUCLEIC ACID SEQUENCES IN YEAST

This invention was made with United States Government support awarded by NIH, Grant Nos. AI23742, AI22813, GM51301 and GM35072. The United States Government has certain rights in this invention.

FIELD OF THE INVENTION

The field of the present invention is methods of producing non-endogenous particles containing nucleic acid sequences in yeast and replicating animal and Nodaviridiae virus nucleic acid sequences in yeast.

BACKGROUND

The understanding of virus-host interactions, including the identity of the host factors with which viruses interact to mediate their replication and cytopathic effects, remains a challenging frontier in virology. For a number of viruses, specific host factors have been implicated in some important infection processes such as cell attachment, DNA transcription and replication, and others. However, for many important virus functions, such as genome replication by (+) strand RNA viruses, the nature of the host factors is not completely known. For most viruses, identification of relevant host factors would be greatly assisted by ready genetic dissection of the host. Particularly effective eukaryotic genetics exists for the yeast *Saccharomyces cerevisiae*, as illustrated by prior identification of host genes required for the maintenance of its endogenous L-A double-stranded RNA virus (Wickner, R. B., eds. Broach, J. R., Pringle, J. and Jones, E. W. (Cold Spring Harbor Press, Cold Spring Harbor, N.Y.), pp. 263–296, 1991). *S. cerevisiae* has been previously shown to support the replication and assembly of other viruses endogenous to fungi (Lhoas, P. *Nature-New Biology,* 236:86–87, 1972; Schmitt, M. J. and Neuhausen, F., *J. Virol.* 68:1765–1772, 1994).

The present invention involves viruses that are non-endogenous to fungi, such as flock house virus (FHV). We show in the Examples that the yeast *Saccharomyces cerevisiae* can support replication of FHV resulting in the production of infectious virions.

Previously, virus-like particles (VLP) with unspecified nucleic acid content have been synthesized in yeast from the plasmid-expressed capsid proteins of other non-endogenous viruses; hepatitis B virus (Valenzuela, P., et al., *Nature* 298:247–350, 1982; Miyanohara, A., et al., *Proc. Natl. Acad. Sci. USA* 80:1–5, 1983; Kniskern, P. J., et al., *Gene* 46:135–141, 1986; Miyanohara, A., et al., *J. Virol.* 59:176–180, 1986), the potyvirus johnsongrass mosaic virus (Jagadish, M. N. et al., *J. Gen. Virol.* 72:1543–1550, 1991), the papillomaviruses HPV-6, HPV-16, HPV-6a, HPV-A18, and CRPV (Hofmann, K. J., et al., *J. Gen. Virol.* 77:465–468, 1996; and references therein), and the picornaviruis polioviruis (Jore, J. P. M., et al., *Yeast* 10:907–922, 1994). Retrovirus human T-lymphotropic virus (HTLV-III) VLP have been produced, although VLP production was inferred from protein processing (Kramer, R. A., et al., *Science* 231:1580–1584, 1986). There is also a report of retrotransposon gypsy "VLP" production, although the VLPs did not resemble "normal" VLPs (Yoshioka, K., et al. *FEBS Letters,* 302:5–7, 1992). Spanning three of four subfamilies in the family Saccharomycetaceae, these non-endogenous VLPs have beer produced in *Saccharomyces cerevisiae, Hansenula polymorpha, Yarrowia lipolytica, Schizosaccharomyces pombe,* and *Pichia pastoris* (Shen, S.-H., et al., *Gene* 84:303–309, 1989; Janowicz, Z. A., et al., *Yeast* 7:431–443, 1991; Hamsa, P. V. and B. B. Chatto, *Gene* 143:165–170, 1994; Sasagawa, T., et al., *Virology* 206:126–135, 1995; Tschopp, J. F., et al., *Biotechnology* 5:479–485, 1987).

A description of increasing yields of tobacco mosaic virus (TMV) with time following incubation of *S. cerevisiae* spheroplasts with TMV virions (not irrefutable evidence) has been reported (Coutts, R. H. A. and Cocking, E. C., *Nature* 240:466–467, 1972).

Systems were recently developed that demonstrate the RNA-dependent replication, transcription and persistence in yeast of derivatives of brome mosaic virus (BMV), a plant-infecting member of the alphavirus-like superfamily (Janda, M. and Ahlquist, P., *Cell* 72:961–970, 1993; Quadt, R., et al., *Proc. Natl. Acad. Sci. USA* 92:4892–4896, 1995; for a simple review see Gallepp, G. *Understanding infection,* UW-Madison College of Agricultural and Life Sciences Science Report, pp. 28–29, 1996). Yeast expressing the viral components of the BMV RNA replicase support replication and gene expression by BMV RNA derivatives. Such RNAs are transmitted through mitosis, so that Ura$^+$ strains can be obtained by transfecting Ura$^-$ yeast with a BMV RNA replicon expressing the URA3 gene. This system provides a basis for selecting mutations in host genes required for BMV RNA replication.

Thus, BMV is the first instance of genomic replication of a non-endogenous virus in *S. cerevisiae*. Attempts to replicate the poliovirus genome in yeast have failed (Coward, P. and Dasgupta, A., *J. Virol.* 66:286–295, 1992; Das, S., et al., *J. Virol.* 68:7200–7211, 1994).

The expression of wild-type BMV RNA3, which contains the BMV coat protein gene, has been reported in conjunction with viral replicase proteins in yeast (Quadt, R., eta. *Proc. Natl. Acad. Sci. USA* 92:4892–4896, 1995).

Flock house virus (FHV) belongs to the Nodaviridae: family of (+) strand RNA viruses, whose members infect invertebrates and vertebrates (for review see Miller, L. K., in *Fields Virology,* eds. Fields, B. N., et al. Lippincott-Raven Publishers, Philadelphia, Vol. I, pp. 549–551, 1996). Several members which infect hatchery-reared fish have recently been identified (Nishizawa, T., et al., *J. Gen. Virol.* 76:1563–1569, 1995).

The 4.5 kb genome of FHV is one of the smallest among animal viruses. FHV particles are infectious to insect cells, and naked FHV genomic RNA is infectious to insect, plant (Selling, B. H., et al., *Proc. Natl. Acad. Sci. USA* 87:434–438, 1990) and mammalian (Ball, L. A., et al., *J. Virol.* 66:2326–2334, 1992) cells.

An FHV plaque assay (Selling, B. H. and Rueckert, R. R., *J. Virol.* 51:251–253, 1984) and neutralizing antibodies (Gallagher, T. M., Ph.D. thesis (University of Wisconsin, Madison), pp. 84–111, 1987) allow sensitive detection of infectious FHV virions.

Infectious transcripts from full-length FHV cDNAs can be produced in vitro (Dasmahaptra, B., et al., *Proc. Natl. Acad. Sci. USA* 83:63–66, 1986) and in vivo (Ball, L. A., *Proc. Natl. Acad. Sci. USA* 91:12443–12447, 1994). Nodaviruses use unique regulatory cis-elements, including Nodaviral-specific RNA replication (Zhong, W., et al., *Proc. Natl. Acad. Sci. USA* 89:11146–11150, 1992; Ball, L. A. and Li, Y., *J. Virol.* 67:3544–3551, 1993; Li, Y. and Ball, L. A., *J. Virol.* 67:3854–3860, 1993; Ball, L. A., *J. Virol.* 69:720–727, 1995) and packaging signals (Zhong, W., et al., supra, 1992; Zhong, W., Ph.D. thesis (University of Wisconsin, Madison, pp. 119–138, 1993), which offer the potential for new mechanisms of RNA and protein expression regulation. FHV RNAs have been used to carry and express heterologous sequences (Zhong, supra, 1993). The ability to package these chimeric RNAs into FHV particles has been demonstrated (Zhong, supra, 1993). In addition, a replicase capable of full in vitro replication of added FHV RNA has been isolated from infected cells (Wu, S.-X. and Kaesberg, P., *Virology* 183:392–396, 1991; Wu, S.-X., et al., *Proc. Natl. Acad. Sci. USA* 89:11136–11140, 1992).

The X-ray structure of FHV (Fisher, A. J. and Johnson, J. E., *Nature* 361:176–179, 1993) and the related black beetle virus (Hosur, M. V., et al., *Proteins: Struct. Funct. Genet.* 2:167–176, 1987) have been solved at 3.0 Å resolution, allowing for insertion of antigens on the particle surface.

The FHV genome is bipartite (FIG. 1A) (Scotti, P. D., et al., *Arch. Virol.* 75:181–190, 1983), with both RNAs packaged in the same particle (Selling, B. H. and Rueckert, R. R., supra, 1984; Gallagher, T. M., supra, 1987). RNA1 (3.1 kb) (Dasmahapatra, B., et al., *J. Mol. Biol.* 182:183–189, 1985) encodes all viral contributions to the FHV RNA replicase and can replicate autonomously (Gallagher, T. M., et al., *J. Virol.* 46:481–489, 1983). RNAL serves as mRNA for protein A (112 kDa) (Friesen, P. D. and Rueckert, R. R., *J. Virol.* 37:876–886, 1981), which contains the GDD amino acid sequence motif characteristic of RNA polymerases and is essential for FHV RNA replication (Ball, L. A., *J. Virol.* 69:720–727, 1995). An RNA1-encoded subgenomic RNA, RNA3 (0.4 kb) (Guarino, L. A., et al., *Virology* 139:199–203, 1984), serves as mRNA for protein B (10 kDa) (Friesen, P. D. and Rueckert, R. R., *J. Virol.* 42:986–995, 1982). Protein B is not required for production of (+) or (−) strand RNA1 or RNA3 (Ball, L. A., supra, 1995). RNA2 (1.4 kb) encodes the virion capsid protein precursor, α (43 kDa) (Friesen, P. D. and Rueckert, R. R., supra, 1981; Dasgupta, R. and Sgro, J.-Y., *Nucl. Acids. Res.* 17:7525–7526, 1989).

Before the present invention, the art of molecular biology lacked a method of producing non-endogenous particles containing nucleic acid sequences in yeast and of replicating animal virus nucleic acid sequences, most particularly Nodaviridae virus nucleic acid sequences, using non-endogenous viral nucleic acid replication proteins in yeast.

SUMMARY OF THE INVENTION

The present invention is a method of synthesizing non-endogenous particles containing nucleic acid sequences in yeast. The method comprises the steps of introducing a non-endogenous packageable nucleic acid sequence and a sequence encoding a suitable non-endogenous capsid protein into yeast cells and inducing assembly of particles, wherein the particle encapsidates at least one nucleic acid molecule.

In one embodiment of the present invention, the particle is an infectious virion.

In one embodiment of the present invention, the method additionally comprises the steps of introducing a replicable nucleic acid sequence and a sequence encoding a suitable nucleic acid replication protein into yeast cells and inducing viral nucleic acid replication.

In one embodiment, the packageable or packageable and replicable nucleic acid sequences or the sequences encoding either the suitable capsid protein comprise non-endogenous virus or non-endogenous retrotransposon sequences, such as animal or plant virus sequences. In another embodiment of the present invention, the packageable or packageable and replicable nucleic acid sequence or the sequence encoding the suitable capsid protein comprise RNA virus sequences. In a preferred form of this embodiment, the packageable or packageable and replicable nucleic acid sequence or the sequence encoding the suitable capsid protein comprise (+) strand RNA virus sequences. In an especially preferred form of this embodiment, the packageable or packageable and replicable nucleic acid sequence or the sequence encoding the suitable capsid protein comprise sequences from a member of the Nodaviridae or Bromoviridae family, such as flock house virus or brome mosaic virus. In a preferred embodiment of the present invention, the packageable or packageable and replicable nucleic acid sequence or the sequence encoding the suitable capsid protein comprises sequences from more than one virus. The packageable or packageable and replicable nucleic acid sequences or the sequence encoding the suitable capsid protein may also comprise non-viral sequences and synthetically created sequences.

The present invention is also a method of replicating animal or a Nodaviridae virus nucleic acid sequences. In a particularly advantageous form of this invention, the replicable nucleic acid sequence or the sequence encoding the suitable nucleic acid replication protein comprise non-viral sequences. Preferably, the non-viral sequence is a protein coding sequence and the coding sequence is expressed.

The present invention is also the product of any of the above-described methods.

It is an object of the present invention to provide infectious virions assembled in yeast cells.

It is another object of the present invention to provide chimeric particles assembled in yeast cells.

It is another object of the present invention to provide chimeric particles comprising chimeric proteins which contain non-viral sequences or peptides.

It is another object of the present invention to provide replication of animal or Nodaviridae virus nucleic acid sequences in yeast cells.

Other objects, advantages and features of the present invention will become apparent after one of skill in the art reviews the specification, claims and drawings.

DESCRIPTION OF THE DRAWINGS

FIGS. 1A–1C diagram the structure of the FHV genome and certain derivatives employed in this study.

DESCRIPTION OF THE INVENTION

1. In General

In the Examples below we describe the first instance of animal or Nodaviridae virus genome replication and the first de novo synthesis of infectious virions by a non-endogenous virus in the yeast *Saccharomyces cerevisiae*. By "non-endogenous" we mean not found in fungi (such as yeast) in the absence of laboratory manipulations.

Our exemplary system, described below in the Examples, uses flock house virus (FHV), the most extensively studied member of the Nodaviridae family of (+) strand RNA animal viruses. Transfection of yeast with FHV genomic RNA induced viral RNA replication, transcription, and assembly of infectious virions. Genome replication and particle synthesis were robust. All replicating FHV RNA species were readily detected in yeast by Northern blotting and yields of infectious virions per cell were similar to those from Drosophila cells.

We also describe in vivo expression and maintenance of a selectable non-viral gene, a yeast marker gene from an engineered FHV RNA derivative dependent on FHV-directed RNA replication.

In a separate example, we also describe the production of BMV (brome mosaic virus) particles containing nucleic acid sequences in yeast.

Our examples with FHV and BMV would allow those of ordinary skill in the art to identify other non-endogenous viruses or retrotransposons and combinations of viral or retrotransposon nucleic acid sequences able to replicate and/or assemble particles containing nucleic acid sequences in yeast and to use these viruses or retrotransposons and their components for analogous applications.

2. Production of Particles Containing Nucleic Acid Sequences

The present invention is a method of synthesizing non-endogenous particles containing nucleic acid sequences, preferably infectious virions, in yeast. Basically, this method comprises the steps of introducing a non-endogenous packageable nucleic acid sequence and a sequence encoding a suitable non-endogenous capsid protein into yeast cell, and inducing particle assembly, wherein at least one nucleic acid sequence, and potentially more than one sequence (including more than one per particle), is encapsidated. By "packageable nucleic acid sequence" we mean a nucleic acid molecule or molecules containing, in addition to other viral or non-viral sequences, a signal or signals which may typically be of viral or retrotransposon origin or synthetic that directs encapsidation by suitable capsid proteins. By "suitable capsid proteins" we mean one or more protein, any of which may typically be derived from viral, multiple viral, nonviral, or synthetic sequences, or any combination thereof, which are capable of packaging the packageable nucleic acid sequence. By "sequence" we mean one or more nucleic acid molecules. For example, suitable capsid proteins containing a packaging signal recognition domain engineered from flock house virus would be chosen to package packageable nucleic acid sequence containing packaging signals engineered from flock house virus.

Preferably, the method additionally comprises the step of inducing viral nucleic acid replication before particle assembly. By "replicable nucleic acid sequence" we mean a nucleic acid molecule or molecules containing, in addition to other viral or non-viral sequences, a signal or signals which may be derived from viral, multiple viral, non-viral, or synthetic sequences that directs replication by suitable nucleic acid replication proteins. By "suitable nucleic acid replication proteins" we mean one or more proteins, any of which may be derived from viral, multiple viral, nonviral, or synthetic sequences, or any combination thereof, which are capable of replicating the replicable nucleic acid sequence. For example, suitable nucleic acid replication proteins containing a replication signal recognition domain engineered from flock house virus would be chosen to replicate replicable nucleic acid sequences containing replication signals engineered from flock house virus.

Preferably, the present invention produces infectious virions. By "infectious virion" we mean one (or more than one in the case of a covirus) particle composed of one or more proteins and nucleic acid sequences, potentially membrane enveloped, capable of transmitting to a susceptible host cell a set of viral genes sufficient to direct the replication and assembly of an infectious virion.

For example, one of our model particle assembly systems described below in the Examples uses a non-endogenous packageable nucleic acid sequence and non-endogenous suitable capsid proteins that comprise natural flock house virus viral control signals and capsid sequences. A non-endogenous packageable nucleic acid sequence may comprise control sequences from more than one virus and may comprise non-viral sequences. For example, our Examples below describe the use of a non-viral yeast sequence as part of the non-endogenous packageable nucleic acid sequence.

Additionally, endogenous yeast viral or retrotransposon sequences may be used as a portion of either the packageable nucleic acid sequence, the sequence encoding suitable capsid protein, the replicable nucleic acid sequence or the sequence encoding suitable nucleic acid replication protein.

In a preferred form of the present invention, a chimeric particle is created. By "chimeric particle" we mean not only a particle composed in part or in whole of "chimeric capsid proteins," but to also particles composed of natural capsid proteins and containing chimeric nucleic acids sequences, or both.

To practice the method of the present invention, one would first create the transgenic yeast cells. By "transgenic" we mean an organism that contains nucleic acid (DNA or RNA) that has been introduced from some other source. As described above and below, this is typically done by introducing a non-endogenous packageable nucleic acid sequence and a sequence encoding a non-endogenous suitable capsid protein into yeast cells. By "introducing" the sequences into yeast cells we mean to include a broad variety of methods known to one of skill in the art of creating a transgenic yeast cell. These methods include transient transfection of nucleic acid (RNA or DNA) unable to be replicated and/or maintained by selection, transformation of nucleic acid replicons (RNA or DNA) able to be replicated and maintained by selection, or integration of DNA into the host chromosomes. Any combination of these methods may be used to introduce different nucleic acid sequences.

Once one has selected various sequence elements combined them in a transgenic yeast cell, one will wish to make sure that an adequate non-endogenous packageable nucleic acid sequence and a sequence encoding a suitable non-endogenous capsid protein have been selected. This can be accomplished by microscopic analysis which can be used to identify particles in yeast extracts and by nuclease resistance of nucleic acids in purified extracts. Hybridization analysis can be used to demonstrate packing of specified nucleic acids within purified particles.

Preferable virus sequences may be taken from animal and plant viruses and viruses of the Nodaviridae and Bromoviridae family. Most preferably, one would use sequences selected from (+) strand RNA viruses, such as flock house virus or brome mosaic virus.

The Examples below demonstrate a preferred method of creating a yeast cell capable of producing an infectious virion. We envision that the method of the present invention would be suitable for any yeast species or strain, preferably of or with affinity to the family Saccharomycetaceae. By "with affinity to" we mean to refer to several "imperfect" yeast which remain to be classified on the basis of reproductive morphology. Preferred yeast species include *Saccharomyces cerevisiae, Pichia pastoris*, and *Schizosaccharomyces pombe*.

3. Replication of Animal and Nodavirus Nucleic Acid Sequences

The present invention is also a method of replicating animal or Nodaviridae nucleic acid sequences in yeast. One must introduce a replicable nucleic acid sequence and a sequence encoding a suitable nucleic acid replication protein into the yeast cell and induce viral nucleic acid replication. The Examples below describe a preferred method of replicating a chimeric flock house virus nucleic acid sequence. Other preferred viral nucleic acid sequences include sequences from Nodaviridae and animal viruses.

An advantageous embodiment of the present invention is the addition of non-viral sequences to the replicating viral sequences. Preferably, these sequences are protein coding sequences and, preferably, the protein coding sequences are expressed. However, the non-viral sequences may also be non-coding sequences such antisense RNA, catalytic RNA, or structural nucleic acid.

Evaluation of replication may be done by characterization of replication intermediates and products of replication by Southern and Northern blotting analysis.

4. Nucleic Acid/Protein Expression Systems

We envision that one of skill in the art would be able to construct a nucleic acid/protein expression system using the methods and products of the present invention. The goal of most "expression systems" is to optimize the regulation and expression level of biologically active proteins; however, for production of particles containing nucleic acid sequences it is also desirable to optimize nucleic acid sequence expression. Such nucleic acid sequences may encode structural, catalytic, or antisense nucleic acid sequences or protein sequences, any of which may be of viral (including multiple viruses) or non-viral origin or combination thereof.

For nucleic acid/protein expression in yeast, vectors could be constructed using standard cloning techniques for in vitro or in vivo production of replicable nucleic acid sequences. In one approach, such a plasmid could contain the desired non-viral coding sequence in a viral RNA cDNA with functional viral RNA replication signals (with or without functional viral RNA packaging signals) flanked on its 5' end by a promoter and on its 3' end by a ribozyme. Note that the positioning and choice of promoter and ribozyme add additional levels of control. The in vitro or in vivo produced replicable nucleic acid sequence would then be introduced into yeast that also express viral nucleic acid replication proteins, resulting in the amplification of the replicable nucleic acid and corresponding increases in protein expression. Expression of the suitable nucleic acid replication proteins could be from a "standard" expression plasmid or via replicable nucleic acid sequence encoding the viral nucleic acid replication protein. Evaluation of replication may be accomplished by characterization of replication intermediates and products of replication by Southern and Northern blotting analysis.

5. Vaccine Production

Vaccines include three general categories, attenuated "live" pathogens, inactivated (killed) pathogens, and chimeric vaccines with an antigenic protein fragment of a pathogen grafted into the shell of a non-pathogenic organism.

For viruses that are pathogenic to commercially important hosts and that replicate in yeast, infectious attenuated virus could be produced in yeast, given clones of the attenuated virus. Viral replicable, packageable nucleic acid sequences could be produced in vitro or in vivo for introduction into yeast.

Similarly, infectious virus for subsequent inactivation could be produced in yeast given clones of pathogenic virus. Alternatively, inactive particles (lacking any or all sequences encoding viral functions required for infectivity) could be produced from replicable (not packageable) nucleic acid sequences encoding suitable capsid proteins and nucleic acid replication proteins (or by substituting packageable, replicable nucleic acid sequences as long as sequences encoding viral functions required for infectivity were not packageable).

In addition, safe, live chimeric particles presenting antigens of specific pathogens can be produced in yeast by the method of the present invention. As a first step, the coding sequence of a desired antigen would be cloned into the clone of the capsid protein of a virus that is not pathogenic to, but able to replicate in, humans or commercially important hosts, such that the antigen would be found on the surface of the mature particle. This clone could then be used to construct DNA vectors for production of replicable and packageable nucleic acid sequences encoding chimeric capsid. Using the methods outlined above, particles containing infectious viral RNA (i.e., a "live" vaccine) which are composed entirely, or in part, of chimeric capsid proteins could be produced. As an example, yeast introduced to packageable, replicable (not packageable) nucleic acid sequences encoding natural capsid protein and nucleic acid replication protein in addition to replicable nucleic acid sequences encoding chimeric capsid would produce a population of virions, composed of various proportions of natural and chimeric capsid proteins, all of which contain infectious nucleic acid sequences. If particles composed entirely of chimeric capsid proteins and containing packageable, replicable nucleic acid sequences encoding chimeric capsid are less infectious than native particles, production of virions with fractional chimeric capsid protein content and containing replicable, packageable nucleic acid sequence encoding natural capsid might result in increased infectivity. Alternatively, non-pathogenic chimeric particles (lacking any or all sequences encoding viral functions required for infectivity) comprising chimeric proteins which contain sequences from viruses pathogenic to humans or commercially important hosts could be produced as described for production of inactive particles of pathogenic viruses.

6. Particle-Mediated Nucleic Acid Delivery (Gene Therapy)

Gene therapy, the delivery of genetic material (either DNA or RNA) to somatic cells, has many potential applications, including treatment of human disease and, e.g., expression of growth hormones in commercially grown fish. Note that by delivery of DNA or RNA encoding antigens of pathogens, "gene therapy vectors" can also be used as vaccines. One of the limitations of gene therapy vectors which are based on transforming viruses is their potential to irreversibly damage the host cell by random or directed integration into the host genome. RNA viruses, such as Nodaviruses, offer the advantages that their replication is cytoplasmic and there is no known mechanism by which their genetic material can be integrated into the host genome.

The delivery of nucleic acid sequences containing packaging or replication signals from any virus to any specific cell type, could be accomplished by packaging the nucleic acid in particles composed of chimeric capsid proteins. Capsid proteins have at least two domains, one which recognizes the packaging signal on the nucleic acid and others which transmit nucleic acid sequences to the cell. Thus, as one example, RNAs containing the flock house virus packaging signal could be delivered to, for example, the human respiratory tract by packaging the RNA into particles composed of chimeric proteins, where the nucleic acid recognition domain is derived from flock house virus and the transmission domains are derived from a human Rhinovirus.

Particles containing packageable, replicable nucleic acid sequences or packageable (not replicable) nucleic acid sequences for delivery to specific host cells could be produced in yeast. Production of packageable, replicable nucleic acid sequences has two possible extensions: the packageable, replicable nucleic acid sequences can be expressed at higher levels during packaging in yeast as described above, and the replicable nucleic acid sequences could be amplified/maintained within a single host cell if co-infected with yeast-produced particles containing, or if co-packaged with packageable, replicable nucleic acid sequences encoding the viral nucleic acid replication proteins.

To encapsidate the packageable, replicable nucleic acid sequences or packageable (not replicable) nucleic acid sequences containing desired sequences into virions composed of natural or chimeric capsid proteins (for tissue targeting), the nucleic acid could be produced in vitro or in vivo for introduction to yeast expressing the capsid protein, as described under vaccine production. If, during production in yeast, nucleic acid replication and capsid proteins are expressed from packageable, replicable nucleic acid sequences, a population of particles containing variable proportions of all packageable nucleic acids would result. Inoculating a host with this mixture would result in amplification (spread from infected to uninfected cells) of all nucleic acid sequences. If, during production in yeast, the nucleic acid replication and capsid proteins are expressed from nucleic acid sequences without packaging signals (including "standard expression vectors"), particles containing only the packageable, replicable nucleic acid sequences or packageable (not replicable) nucleic acid sequences containing the desired sequences would result.

7. Biological Pesticide Production

Alternatives to chemical pesticides are increasingly attractive. Many Nodaviruses were originally isolated from dying insect larvae (Miller, L. K., in Fields *Virology*, eds. Fields, B. N., et al. (Lippincott-Raven Publishers, Philadelphia) Vol. I, pp. 549–551, 1996; and references therein) with the hope of developing them as biological pesticides. For those viruses (including viruses outside the Nodaviridae family) which could be used directly as pesticides (i.e., pathogenic only to defined hosts, rapid lethality to the host, etc.), commercial quantities of infectious virions could be produced in yeast, as described above under vaccine production. For those viruses which could not be used directly as effective pesticides, but which are pathogenic to insects, their lethality could be increased or made species-specific by engineering suitable packageable, replicable nucleic acid sequences or packageable (not replicable) nucleic acid sequences to express genes for toxic proteins, including proteins that are selectively toxic to insects, or to express toxic RNAs (e.g. antisense RNA, catalytic RNA, etc.), including RNAs that are selectively toxic to certain insects, as described above under particle-mediated nucleic acid delivery.

EXAMPLES

Here we demonstrate that *S. cerevisiae* spheroplasts transfected with FHV RNA support full replication of FHV, including assembly of infectious virions, and we describe a system for in vivo expression and maintenance of heterologous marker genes dependent on FHV RNA replication.

We also demonstrate that *S. cerevisiae* introduced to BMV-derived RNA support production of BMV-derived particles containing RNA.

Abbreviations: BMV, brome mosaic virus; DI, defective interfering; FHV, flock house virus; hpt, hours posttransfection; ORF, open reading frame; PCR, polymerase chain reaction; PFU, plaque forming units.

1. Materials and Methods

Plasmids. To construct p1R and p1(fs)R (see Results), the 5.3 kb Sca I-Nar I fragment of pFHV1[1,0] (Ball, L. A., supra, 1994), containing an FHV RNA1 cDNA flanked one nucleotide from its 5' end by a T7 promoter and zero nucleotides from its 3' end by a hepatitis delta virus ribozyme and a T7 terminator, was transferred to the 3.0 kb Nar I-Sca I fragment of the yeast shuttle plasmid YEplac112 (Gietz, R. D. and Sugino, A., *Gene* 74:527–534, 1988). For p1(fs)R, the Eag I site at position 373 of the FHV RNA1cDNA was digested, filled in, and re-ligated. The 0.17 kb Sac I fragment containing the T7 terminator was deleted from p1R and p1(fs)R.

To construct pDU (see Results), a 0.9 kb Sac I fragment containing a modified URA3 gene from YEp24 (Bolstein, D., et al., *Gene* 8:17–24, 1979; Zhong, W. and Rueckert, R. R., *J. Virol.* 67:2716–2722, 1993) was transferred to the Sac I site of pBS-DI634 (Zhong, W. and Rueckert, R. R., supra, 1993). The 5' end of the modified gene was a 238 bp Sac I-Nco I fragment of a product amplified by polymerase chain reaction (PCR) with the primers 5'-GCGGAGCTCTGTCGAAAGCTACATATAAGGAA-3' (SEQ ID NO:1) and 5'-AGCGGCTTAACTGTGCCCTCC-3' (SEQ ID NO:2), and the 3' end was a 649 bp Nco I-Sac I fragment with a Sac I linker inserted at the Sma I site in the 3' noncoding region. To construct pDUΔ3', the 106 bp Msc I-Bam HI fragment of pDU containing the 3' 100 bp of the DI634 cDNA was deleted.

Figure 1:
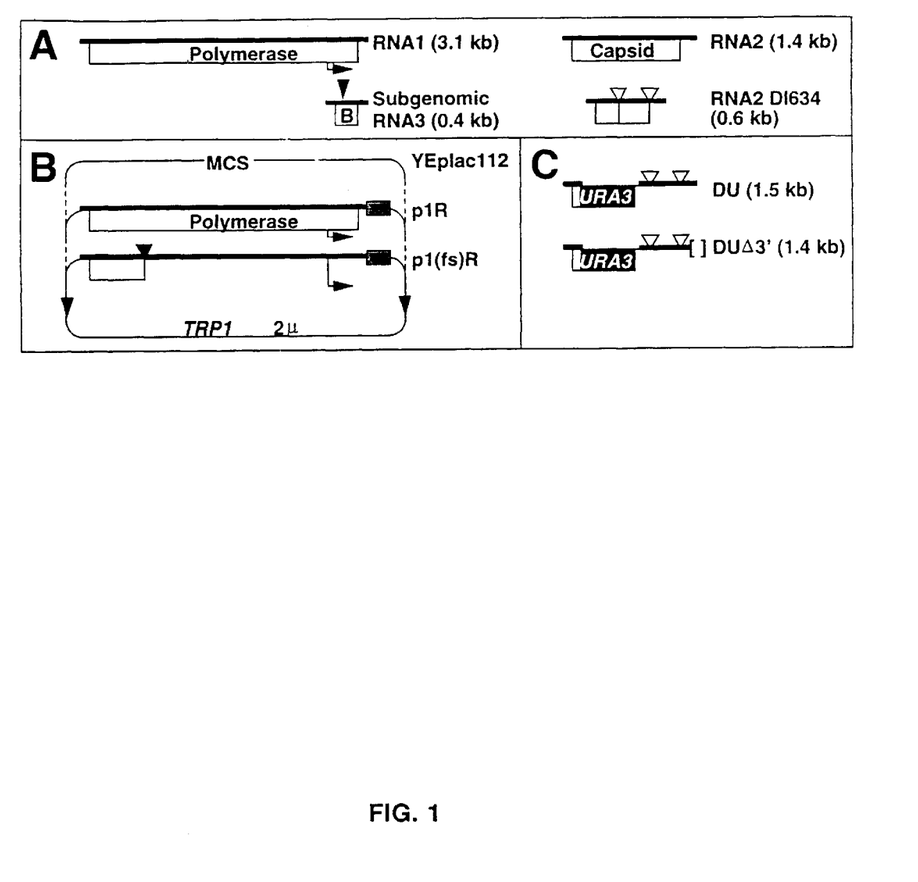
FIG. 1A is a schematic drawing of the FHV genomic RNA1 and RNA2.
FIG. 1B is a schematic drawing of plasmids YEplac112, P1R, and p1(fs)R.
FIG. 1C is a schematic drawing of DU and DUΔ3' RNAs.

FIG. 1 diagrams the structure of the FHV genome and derivatives employed in this study.

FIG. 1A is a schematic drawing of FHV genomic RNA1 and RNA2. Subgenomic RNA3 is shown below RNA1. A derivative of RNA2, defective interfering RNA 634 (DI634) is shown below RNA2. Open boxes represent ORFs and lines represent nontranslated regions. The bent arrow below RNA1 represents the 5'-most nucleotides of RNA3. ORF A (polymerase) and ORF B overlap in different frames. The open triangles above DI634 represent two deleted RNA2 sequences.

FIG. 1B is a schematic drawing (not to scale) of plasmids YEplac112, P1R, and p1(fs)R. MCS indicates the multiple cloning site of YEplac112. The full-length FHV RNA1 cDNA is depicted as a heavy line. A hepatitis delta virus ribozyme cDNA is denoted with a shaded box. The filled triangle in p1(fs)R represents a 4 nucleotides insertion following nucleotides 377. The relative position of the TRP1 gene and yeast 2μ origin of replication are indicated.

FIG. 1C is a schematic drawing of DU and DUΔ3' RNAs. Sequences derived from FHV DI634 are represented as heavy lines. The URA3 ORF, indicated by the filled box, is fused in-frame to the first twelve codons of the FHV capsid protein, indicated by the open box. The last 100 nucleotides of DU are deleted in DUΔ3', as indicated by the brackets.

In vitro transcripts. Unlabeled in vitro transcripts were generated using an Ampliscribe kit (Epicenter Technologies), treated with DNAse I, and purified by phenolchloroform extraction and sephadex G50 (Pharmacia)

spin column chromatography. (+) DU and (+) DUΔ3' contained 4 non-viral nucleotides at their 3' ends.

Strand-specific $^{32}$P-labled in vitro transcripts were generated as described (Kroner, P. and Ahlquist, P., in *Molecular Plant Pathology*, eds. Gurr, S. J., et al. (IRL Press, Oxford), Vol. 1, pp. 23–34, 1992). The probes for (−) and (+) RNAs 1 and 3 corresponded to or were complementary to nucleotides 2718 to 3064 of FHV RNA1. The probe for (−) RNA2 corresponded to nucleotides 425 to 1080 of FHV RNA2. The probe for (+) RNA2 was complementary to nucleotides 62 to 1400 of FHV RNA2. The probe for (−) URA3 corresponded to the entire 804 nucleotides URA3 open reading frame (ORF) plus 140 nucleotides downstream. The probe for (+) URA3 was complementary to the 3' 598 nucleotides of the URA3 ORF plus 140 nucleotides downstream.

Transformation and transfection of yeast. Plasmid DNAs were introduced into YPH500 (α ura3-52 lys2-801 ade2-101 trpl-Δ63 his3-Δ200 leu2-Δ1) cells as described (Ito, H., et al., *J. Bacteriol.* 153:163–168, 1983). FHV virion RNA and in vitro transcribed RNAs were transfected into YPH500 spheroplasts using PEG and CaCl$_2$ (Russell, P. J., et al., *Nucl. Acids Res.* 19:4949–4953, 1991.; Janda, M. and Ahlquist, P., supra, 1993). Yeast were grown at 26° C. in media selective for plasmid and RNA replicon maintenance.

Analysis of FHV-derived particles, RNA, and DNA. Yeast spheroplasts were pelleted at 5K rpm for 5 minutes, resuspended in FHV buffer (50 mM NaHEPES (pH 7.0), 0.1% BME, 0.1% BSA) and stored at −80° C. The lysate was thawed and cleared of cell debris by centrifuging at 9K rpm at 4° C. for 30 minutes. Total infectious virion content was determined by assaying the cleared culture and spheroplast lysate for plaque formation on Drosophila cell monolayers.

Total yeast RNA was extracted with phenol/chloroform as described (Carlson, M. and Botstein, D., Cell 28:145–154, 1982) except that glass beads were omitted for spheroplasts. Total Drosophila RNA was isolated with phenol/chloroform (Zhong, W. and Rueckert, R. R., supra, 1993) 20 hours after transfection. URA3 sequences were amplified from 1.25 μg total yeast DNA or 0.25 ng YEp24 as described (Janda, M. and Ahlquist, P., supra, 1993) except that Taq Extender (Stratagene) was used.

For Northern analysis, RNAs were denatured with glyoxal (Kroner, P. and Ahlquist, P., supra, 1992) and electrophoresed on a 0.8% agarose-10 mM phosphate gel. For Southern analysis, PCR products were electrophoresed on a 1% agarose gel. Nucleic acids were transferred to Zetoprobe (BioRad) membranes which were prehybridized for four hours, hybridized overnight in 50% formamide at 60° C. with 5×10$^6$ CPM/ml per probe, and washed at 60° C. following the manufacturer's protocols. Quantitative results were obtained with a Molecular Dynamics Phosphor Imager digital radioactivity imaging system (Sunnyvale, Calif.).

Drosophila cells. The WR strain (Friesen, P. D. and Rueckert, R. R., supra, 1981) of Drosophila cells was propagated (Zhong, W. and Rueckert, R. R., supra, 1993), infectious virions were assayed on Drosophila cell monolayers (Schneemann, A., Zhong, W., Gallagher, T. M. and Rueckert, R. R., *J. Virol.* 66:6728–6734, 1992), and FHV particles were treated with neutralizing FHV antibody (Gallagher, T. M., supra, 1987) as described previously. 2×10$^6$ Drosophila cells were lipofectin-transfected (Zhong, W. and Rueckert, R. R., supra, 1993) with 40 ng gel-purified viral RNA1, or 40 ng gel-purified viral RNA1 plus 100 ng in vitro-transcribed DU RNA.

BMV-derived Plasmids. Plasmids pB1CT19 and pB2CT15 express the BMV replication proteins 1a and 2a, and have been described in (Janda, M. and P. Ahlquist, Cell 72:961– 970, 1993). Plasmid pB3RQ39 expresses a wild-type, replicatable BMV RNA3 and has been described in (Quadt, R., et al., *Proc. Natl. Acad. of Sci. USA* 92:4892–4896, 1995); a similar plasmid, pB3MI10, was used for some early experiments. Plasmid pMKCP3 expresses the BMV capsid protein under the control of the yeast GAL1promoter and was constructed by ligating four DNA fragments, the 0.7 kb EcoR I-BamH I fragment of pBM272 (Johnston, M. and R. W. Davis, *Mol. Cell. Biol.* 4(8):1440–1448, 1984) (encoding the yeast GAL1 promoter), the 0.3 kb HindIII-Sph I fragment of pAAH5 (Vainio, A. E. I., ADH promoter region, Genbank accession number 25479, Genbank, 1993) (encoding the yeast ADH polyadenylation signal), the 5.5 kb EcoR I-Sph I fragment of YCplac33, and the 0.7 kb Bgl II-Hind III fragment derived from the plasmid pBTP8 (Janda, M., et al. *Virology* 158:259–262, 1987), by insertion of the linker comprising the oligonucleotides 5'-TCGAGATCTTTAAAATG-3' (SEQ ID NO:3) and 5'-TCGACATTTTAAAGATC-3' (SEQ ID NO:4) into the Sal I site.

Figure 4:
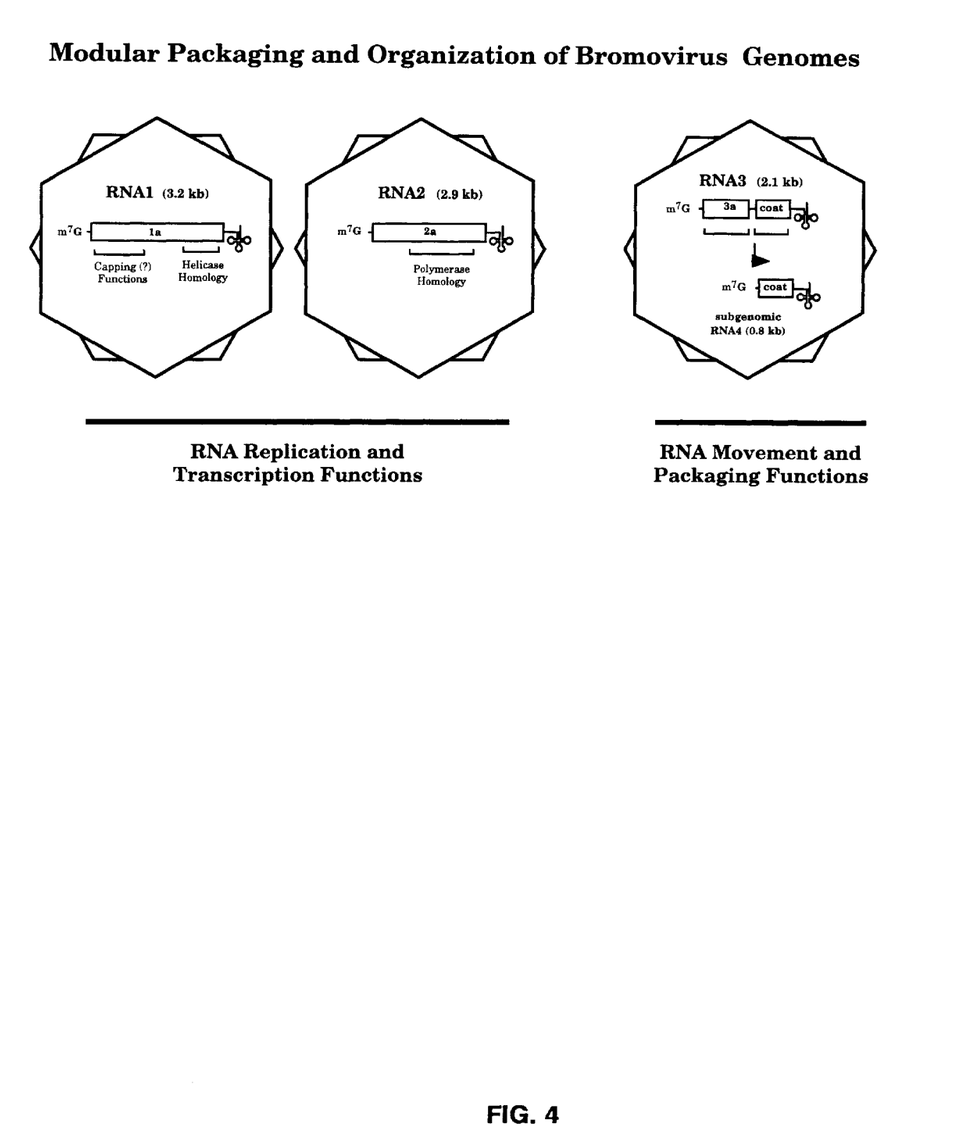
FIG. 4 shows the modular packaging and organization of the BMV genome.

FIG. 4 shows the modular packaging and organization of the BMV genome (derived from Ahlquist, P., *Curr. Opi, Gen., Dev.* 2:71–76, 1992 and Lane, L., in Handbook of Plant Virus Infections and Comparative Diagnosis ed. E. Kurstak, Elsevier/North-Holland Biomedial Press, Amsterdam 1981).

Figure 5:
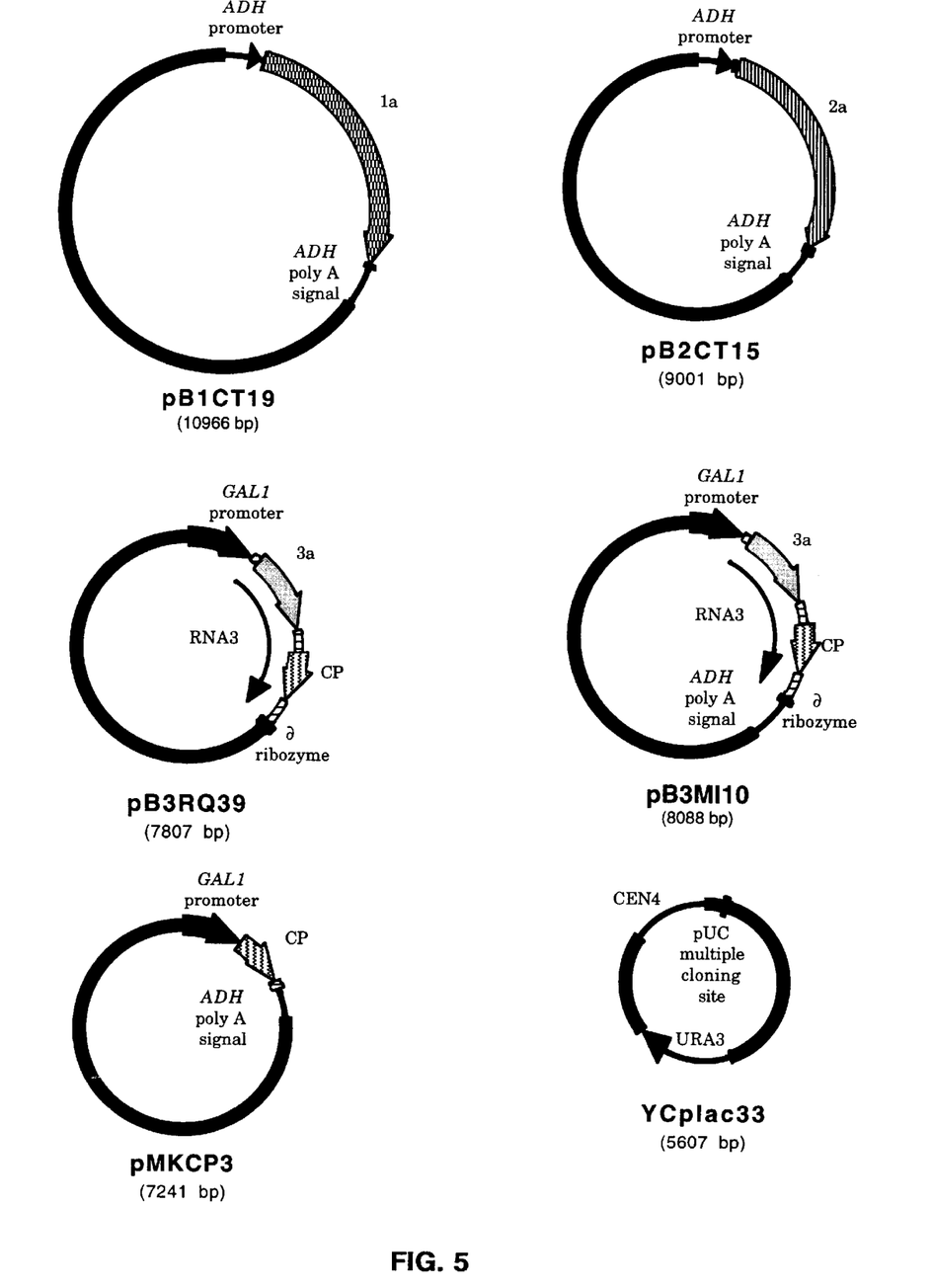
FIG. 5 is a schematic drawing of the plasmids pB1CT19, pB2CT15, pB3RQ39, pB3MI10, pMKCP3, and YCplac33.

FIG. 5 is a schematic drawing (not to scale) of BMV derivatives employed in this study; plasmids pB1CT19, pB2CT15, pB3RQ39, pB3MI10, pMKCP3, and YCplac33.

Isolation and analysis of BMV-derived particles. Expression of RNA3 and the capsid protein were induced by growth with galactose as the sole carbon source (Guthrie, C. and G. Fink, *Methods in Enzymology*, Vol. 194. *Guide to Yeast Genetics and Molecular Biology*, Methods in Enzymology, San Diego, Academic Press, Inc., 1991). Yeast (YPH500) were grown at 30° C. to OD600 of approximately 0.7 in liquid media (500 ml), harvested by centrifugation (5 minutes, 3000×g), washed once in water, washed once with ST (1M sorbitol, 50 mM Tris-HCl, pH 7.5), and resuspended in 5 ml STM (1M sorbitol, 50 mM Tris-HCl, pH 7.5, and 10 mM 2-mercaptoethanol). Cell walls were digested by addition of 5000 units of lyticase (Sigma), and incubation at 30° C. for 2.5 hours with gentle shaking. Cells were lysed by vigorous shaking for 5 minutes following the addition of 10 grams of glass beads (400–600 μm; Sigma), 5 ml VSB (100 mM Na acetate, pH 5.0, 1 mM EDTA, 10 mM MgCl$_2$, 5 mM CaCl$_2$), and 10 ml CHCl$_3$. Clarified cell lysate was obtained by centrifugation at 30,000×g for 15 minutes at 4° C. Particles were pelleted from cell lysate after centrifugation for w$^2$t=1.5×10$^{11}$ in a Beckman Ti70 rotor at 10° C., resuspended in 0.5 ml VSB, and purified by centrifugation through a 5–40% linear sucrose gradient in a Beckman SW41 rotor for 1.5 hours at 40,000 rpm. Particle containing fractions were collected and the particles pelleted by ultracentrifugation.

Analysis of protein and nucleic acids by SDS-PAGE, agarose gel electrophoresis, and blotting were essentially by standard protocols (Ausubel, F. M., et al., *Current Protocols in Molecular Biology*, New York, John Wiley & Sons, Inc., 1987–1996), and (Sambrook, J., et al., *Molecular Cloning—a laboratory manual*, Cold Spring Harbor, Cold Spring Harbor Laboratory Press, 1989). Western (protein) blots were probed with polyclonal sera against BMV capsid protein, and detected with the ECL chemiluminesence kit (Amersham). Total particle RNA was imaged by staining with ethidium bromide and subsequent fluorescent photography. Northern blots were analyzed with a Molecular Dynamics phosphorimaging system and accompanying software.

Nuclease sensitivity of the RNA associated with particles was determined by incubation of approximately 10 μg of particles with 220 units of S1 nuclease (Pharmacia) at 37° C. for one hour in ½×VSB plus 10 mM $ZnCl_2$. Nuclease was inactivated by addition of EDTA to 20 mM, and RNA purified by phenol/$CHCl_3$ extraction and precipitation with isopropanol.

Determinations of sedimentation values was performed in ½×VSB at 20° C. with a Beckman XLA analytical ultracentrifuge.

In collaboration with Dr. Norman Olson and Dr. Timothy Baker (Department of Biological Sciences, Purdue University), digital reconstructions of plant-derived and yeast-derived particles were made from cryo-electron micrographs of frozen, hydrated particles as described in Speir, 1995 #142, providing a three-dimensional image (at approximately 25 Å resolution) of the particles for comparison.

2. Results

Infectious FHV virions from FHV RNA-transfected yeast. As a sensitive assay for biological activity of FHV RNAk in yeast, yeast spheroplasts were transfected with phenol-extracted FHV genomic RNA1 and RNA2 and, at intervals, tested for infectious FHV virion production by plaque assay on Drosophila cell monolayers.

Figure 2:
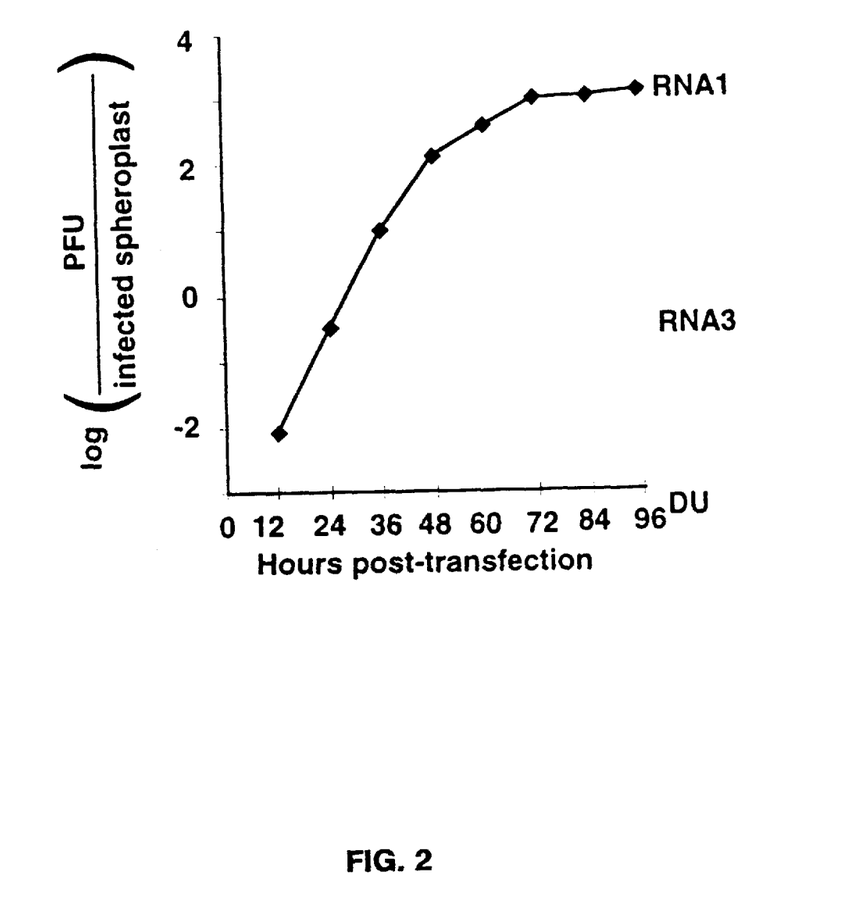
FIG. 2 is a single step FHV growth curve in FHV virion RNA-transfected yeast spheroplasts.

FIG. 2 is a single step FHV growth curve in FHV virion RNA-transfected yeast spheroplast. $5 \times 10^8$ yeast spheroplasts were transfected with 5 μg FHV virion RNA, resuspended in 10 ml media and incubated 96 hours. At 12 hour intervals, aliquots were assayed for plaque forming units (PFU) on Drosophila cell monolayers. The total number of PFU per ml divided by the number of infected spheroplasts per ml (as determined by endpoint dilution assay: see Results) are plotted on a log scale versus hours post-transfection (hpt).

As seen in FIG. 2, plaque forming units (PFU) were recoverable by 12 hours post-transfection (hpt), increased beyond 60 hpt, and plateaued by 72 hpt. These PFU corresponded to infectious FHV virions, as their infectivity was abolished by incubation (1 hour, 37° C.) with a 1:10,000 dilution of FHV-neutralizing antiserum, while 0.1 mg/ml ribonuclease A had no effect.

Consistent with the expected intracellular origin, 90% of these PFU described in FIG. 2 were recoverable only after deliberate lysis of the yeast. The exponential increase in FHV PFU between 0 and 48 hpt (see log scale in FIG. 2) suggested that these infectious virions resulted from encapsidating the products of significant FHV RNA replication in yeast, rather than simply translating and encapsidating the input inoculum RNA. Conclusive evidence of this, including temporal and quantitative correlation between newly synthesized RNA and PFU accumulation, is given below.

In parallel controls, spheroplasts were mock-transfected or transfected with intact infectious FHV virions. PFU were never detected in mock-transfected spheroplasts. Under the conditions used, there was no evidence of significant viral replication in spheroplasts transfected with FHV infectious virions, rather than FHV RNA. PFU were recovered in the media and the number of PFU remained constant from zero to four days post-transfection. Thus, under the conditions of the experiment, extracellular infectious virions were stable but unable to infect new spheroplasts.

Transfection efficiency and yield of PFU. The PFU yields suggested that both transfection efficiency and PFU yield per infected spheroplast were high. To determine both parameters, an endpoint dilution experiment was conducted. Transfected spheroplasts were serially diluted in growth medium and multiple aliquots of each dilution placed in wells of microtiter plates at zero hpt. Plates were affixed to a cell culture roller and incubated at 26° C. At 72 hpt, spheroplasts were lysed and lysates from each well were assayed for PFU. In two independent transfections, at a dilution corresponding to 125 spheroplasts per well, PFU were detected in only 17 of 50, and 14 of 50, wells. Assuming Poisson's distribution, 0.3% of the spheroplasts were infected and the 31 wells with PFU contained 37 infected spheroplasts. Based on the sum of PFU from per wells ($7.1 \times 10^4$ PFU), the average yield was 2,000 PFU per infected spheroplast. This yield per transfected spheroplast correlates well with that in the transfection timecourse experiment at and beyond 72 hpt (FIG. 2), which was calculated assuming the same transfection efficiency.

Replication of FHV RNA in yeast. Proof that progeny infectious virions resulted from true replication, rather than repackaging of the inoculum, was obtained by hybridizing Northern blotted total RNA with strand-specific probes. No hybridization of FHV probes to total RNA extracted from mock-transfected or infectious virion-transfected spheroplasts was observed.

The first product of genomic replication is (−) RNA, which is not present in the inoculum. We performed a Northern analysis to demonstrate FHV genome replication and transcription in FHV virion RNA-transfected yeast spheroplasts. Total RNA was extracted from spheroplasts in the culture described in FIG. 2. RNAs were denatured with glyoxal, electrophoresed on an agarose-phosphate gel, transferred to a nylon membrane, hybridized to the indicated strand-specific $^{32}$P-labeled in vitro transcripts, and exposed to a Phosphor Imager imaging plate.

Northern analysis of (−) strand FHV RNA included lanes 1–9 containing one-fifth of the total RNA isolated from spheroplasts in 1 ml of culture at the indicated time point, lane 10 containing 4 ng each of (+) strand FHV RNA1 and RNA2 in vitro transcripts, lane 11 containing 0.08 ng each of (−) strand FHV RNA1 and RNA2 in vitro transcripts and lane 12 containing total RNA extracted from Drosophila cells 20 hours after transfection with FHV virion RNA. Four ng of total yeast RNA was used as a carrier in lanes 10–12. The blot was hybridized simultaneously to two probes complementary to (−) strand FHV RNA3 and RNA2.

As seen in the Northern blot described above, (−) strand-specific probes first revealed genomic-sized (−) RNAs above background levels at 24 hpt (lane 3). (−) RNA levels increased until 72 hpt (lanes 4–7) and decreased somewhat by 84 and 96 hpt (lanes 8 and 9). A band comigrating with (−) subgenomic RNA3 appeared by 12 hpt (lane 2) in longer exposures, increased until 60 hpt (lanes 3–6) and decreased somewhat by 96 hpt (lanes 7–9).

In addition to (−) RNA1, (−) RNA2, and (−) RNA3 -sized RNAs, two other RNA species were visible by 60 hpt lanes 6–9. Both were also detected in longer exposures of total RNA extracted from transfected Drosophila cells (lane 12) and both hybridized to (−) RNA2 strand-specific probes. The larger band may represent incompletely denatured RNA2 replicative intermediate. The smaller band may represent a degradation product or (−) RNA of newly formed defective interfering (DI) RNA. DI RNAs readily arise from plaque-purified Nodaviruses (Gallagher, T. M., supra, 1987; Guarino, L. A., et al., supra, 1984).

We also performed a Northern analysis as described above except that 4-fold less RNA was loaded per lane, the blot was hybridized simultaneously to two probes complementary to (+) strand FHV RNA3 and RNA2, and the image was printed at one-third the intensity level. As seen in this Northern, (+) strand-specific probes revealed low levels of input genomic (+) RNA1 and (+) RNA2, but not subgenomic (+) RNA3, a product of replication, at zero hpt (lane 1). The levels of genomic-sized RNAs decreased between 0 and 24 hpt (lanes 2 and 3), began to increase at 36 hpt (lane 4), then plateaued at 72 hpt (lanes 7–9). At 12 hpt (lane 2), in longer exposures, a band comigrating with subgenomic RNA3 (lane 12) could be detected. The level of this RNA increased from 12 to 72 hpt, then plateaued (lanes 3–9).

Figure 3:
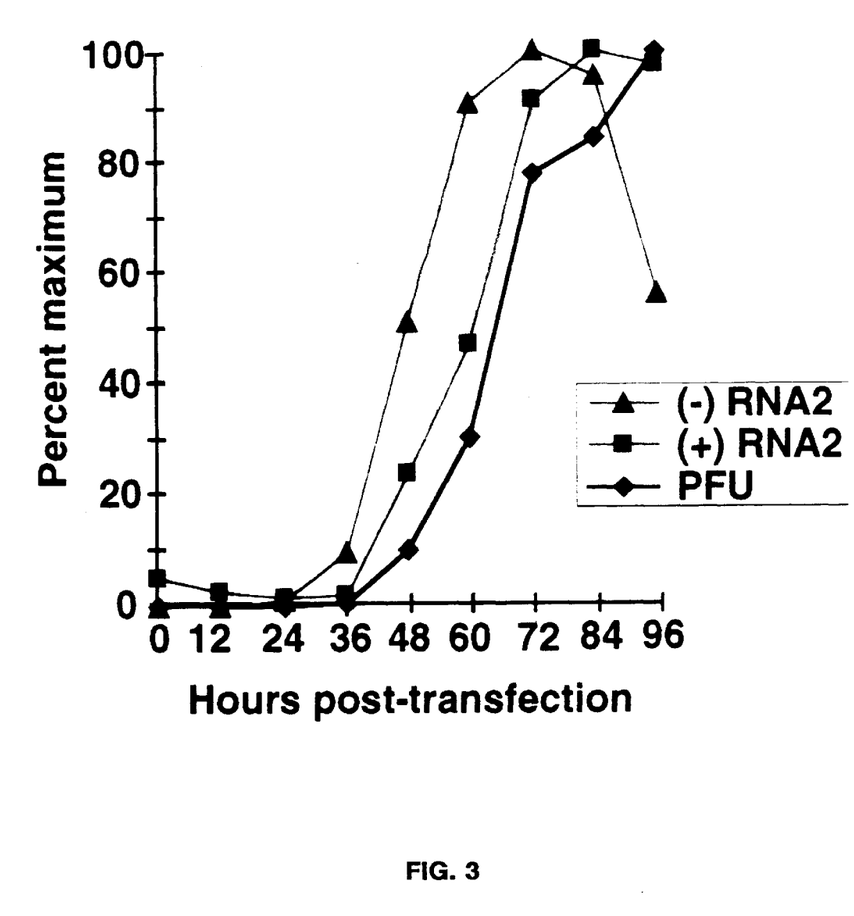
FIG. 3 is a graph of accumulation of FHV (−) RNA2, (+) RNA2, and plaque forming units (PFU) (from FIG. 2), as percent maximum of each, versus hours post-transfection.

FIG. 3 is a graph of the accumulation of FHV (−) RNA2, (+) RNA2 and PFU (FIG. 2), as percent maximum of each, versus hours post-transfection. As seen in FIG. 3, FHV (−) and then (+) RNA accumulation foreshadowed PFU accumulation in yeast. Measurements of PFU and RNA show that the vast majority of yeast-derived FHV particles must contain FHV RNAs synthesized in yeast. The infectious virion yield at 72 hpt and beyond was $2 \times 10^8$ PFU per ml of culture. Unless yeast-derived FHV particles had higher specific infectivity than those from Drosophila cells, which have a particle to PFU ratio of 320 (Selling, B. H. and Rueckert, R. R., et al., supra, 1984; Schneemann, A., et al., supra, 1992), this corresponded to 160 ng encapsidated FHV RNA per ml.

In comparison, the total level of cell-associated genomic RNA per ml of culture was ~40-fold less than this at zero hpt, but only ~3-fold less at 72 hpt (as determined by Phosphor Imager quantification of the bands in lanes 1 and 7 of the Northern blot described above, and similar experiments). The final 3-fold difference may reflect, in part, losses during RNA extraction.

Selection of uracil prototrophs from yeast transfected with an RNA replicon. Because yeast support FHV RNA replication, a system for in vivo expression and maintenance of heterologous markers dependent on FHV genomic replication was developed. To provide FHV trans-acting replication functions, plasmid p1R (FIG. 1B) was designed with an intact FHV RNA1 cDNA one nucleotide downstream of the bacteriophage T7 RNA polymerase promoter, and with a hepatitis delta virus ribozyme cDNA positioned to cleave primary transcripts at the exact 3' end of FHV RNA1 (Ball, L. A., supra, 1994). A control plasmid, p1(fs)R (FIG. 1B), differs from p1R by a frameshift 10% into the polymerase gene. Control experiments showed that inclusion of a plasmid expressing T7 RNA polymerase in *S. cerevisiae* (Benton, B. M., et al., *Mol. Cell. Biol.* 10:353–360, 1990) was inconsequential for all experiments described below. Its function was presumably replaced by cellular polymerases acting at cryptic promoters in P1R and p1(fs)R. Similar results have been reported for FHV RNA2 cDNA constructs in mammalian cells (Ball, L. A., supra, 1994).

To express and maintain a heterologous marker in vivo, RNA DU (FIG. 1C) contains the yeast URA3 ORF fused to the first twelve codons of the FHV capsid protein precursor in the context of DI634, a naturally occurring, efficiently replicating DI RNA derived from RNA2 (Zhong, W. and Rueckert, R. R., supra, 1993). A control variant of DU, DUΔ3' (FIG. 1C), lacked the 3' 100 bp of FHV RNA2, which are necessary for its replication.

To determine if DU could be replicated, express ORA3, and persist in yeast, YPH500 (ura3-52) spheroplasts containing p1R or p1(fs)R were transfected with DNAse I-treated, capped in vitro transcripts of DU, DUΔ3' or B3URA3. B3URA3 is a BMV RNA3 derivative able to replicate and express URA3 in yeast expressing BMV replicase genes (Janda, M. and Ahlquist, P., supra, 1993), but which lacks cis-elements required for FHV-directed replication. As seen in Table I, below, consistent with a requirement for both the trans and cis-components of FHV genomic replication, no colonies were obtained when DU RNA was transfected into spheroplasts containing p1(fs)R, or when spheroplasts containing p1R were transfected with DUΔ3' or B3URA3. Consistent with replication and inheritance of the DU RNA replicon, Ura$^+$ colonies were obtained following DU RNA transfection into spheroplasts containing p1R.

TABLE I

Representative results for selection of uracil prototrophs following transfection of ura3–52 yeast with the indicated RNA.

| Yeast strain | transfected with | Ura$^+$ colonies |
|---|---|---|
| p1R | 100 ng DU | 4.5 |
|  | 1,000 ng DU | 36 |
|  | 1,000 ng DUΔ3' | 0 |
|  | 2,000 ng B3URA3 | 0 |
| p1 (fs) R | 1,000 ng DU | 0 |

$5 \times 10^7$ YPH500 (ura3–52) spheroplasts containing p1R or p1 (fs) R (see FIG. 1) were transfected with DU, DUΔ3' (see FIG. 1), or B3URA3 (see 2) DNAse I-treated in vitro transcripts. The spheroplasts were then plated in regeneration agar lacking uracil to select for Ura$^+$ prototrophs. The numbers of colonies are the averages of two independent experiments.

Absence of wild-type UA3 DNA in prototrophs. To determine if the above Ura$^+$ phenotype was due to unexpected alteration at the level of DNA, a PCR assay was used. The inactivating ura3-52 lesion in the starting yeast is a Ty transposon insertion into the URA3 coding region (Rose, M. and Winston, F., *Mol. Gen. Genet.* 193:557–560, 1984). Primers that anneal 28 bp 37 of the URA3 initiation codon and 20 bp 5' of the termination codon allowed simultaneous amplification of a 758 bp URA3 amplimer and a 6.5 kb ura3-52 amplimer. PCR products amplified from total DNA extracted from relevant yeast strains were analyzed by Southern blot analysis with a URA3 probe.

A 6.5 kb band corresponding to the expected ura3-52 amplimer was detected in PCR products from all strains derived from YPH500 (ura3-52). This band was not detected in PCR products from a control yeast strain with a wild-type chromosomal URA3 locus. A 0.8 kb band corresponding to the expected URA3 amplimer was only detected in PCR products from YPH500 (ura3-52) cells containing YEp24, a control plasmid with a wild-type URA3 gene, or from a control yeast strain with a wild-type chromosomal URA3 locus. This band was not detected in PCR products from DU-transfected, Ura$^+$ cells. Two additional high molecular weight bands of unknown origin were also detected in PCR products from cells containing the empty p1R cloning vector (YEplac112) or YEp24. As these bands were not present in samples from DU-transfected cells, they do not confuse the results.

Presence of replicating FHV RNAs in prototrophs. To test for possible maintenance of DU RNA by FHV-directed RNA replication, total RNA was extracted from DU RNA-transfected, Ura$^+$ yeast strains for Northern blotting. (+) and (−) strand-specific FHV RNA3 probes revealed no detectable bands in total RNA from yeast cells containing p1R progenitor YEplac112 or in total RNA from mock-transfected Drosophila cells. RNA species corresponding in size to (+) and (−) strand RNA1 and RNA3 were detected in total RNA extracted from yeast containing p1R, but not p1(fs)R. An RNA species migrating just above (+) RNA1 was present in total RNA extracted from cells containing p1R or p1(fs)R. This species may represent a transcript derived from p1R and p1(fs)R by upstream initiation by cellular DNA-dependent RNA polymerase.

(+) and (−) strand-specific URA3 probes revealed no bands in total RNA from any YPH500 (ura3-52) yeast cells not transfected with DU RNA, or in total RNA from mock- or RNA1-transfected Drosophila cells. However, total RNA extracted from Drosophila cells transfected with RNA1 and DU RNA or from DU-transfected Ura$^+$ yeast contained (+) and (−) DU-sized RNA bands. Therefore, DU RNA-transfected, Ura$^+$ yeast prototrophs, at least 30 generations after transfection, contain RNAs that hybridize to (+) and (−) URA3 probes and have mobilities indistinguishable from DU RNA replicated in Drosophila cells.

Particles containing BMV-derived RNA are formed in yeast expressing only the BMV capsid protein. Particles can be prepared from yeast which express only the BMV capsid protein expressed from pMKCP3. These particles have an approximate S value of 61 in ½×VSB at 20° C. Particles prepared from the sucrose gradient are highly purified and their protein content consists only of BMV capsid protein, as evident by the lack of contaminating bands in a coomassie blue stained SDS-PAGE gel. Packaging of RNA associated with particles was demonstrated by co-purification of the RNAs with the capsid protein through the scheme detailed above and by demonstration that these RNAs are extremely nuclease resistant; under these conditions 10 µg of added tRNA was largely degraded. Particle-associated RNA, as visualized by staining and fluorescent photography of RNA electrophoresed through an agarose gel, shows a major band at 0.9 kb. Northern analysis verifies that this band is capsid protein messenger RNA, which has been selectively packaged into particles. This selectivity is reminiscent of in vivo packaging in the natural infection.

Particles assembled from the BMV capsid protein expression system in yeast can package other BMV-derived RNAs. When another virus-derived RNA is present in yeast cells expressing the capsid protein, it is also packaged. One of several examples is the directed packaging of the RNA3 transcript product of the plasmid pB3RQ39. Coomassie staining of an SDS-PAGE gel reveals only viral capsid protein in sucrose gradient purified preparations of these particles. These particles have an S value of approximately 66 in ½×VSB at 20° C., consistent with the expected increase in RNA content relative to the particles from yeast expressing only the capsid protein. Gel electrophoresis shows that in addition to the coat protein message band, a band with approximately equal intensity is seen which comigrates with authentic RNA3 from plant-derived particles. Northern analysis has verified that this band consists of RNA3 transcripts from pB3RQ39. This is a physical demonstration of directed packaging in trans of a viral RNA by the corresponding viral capsid protein in the absence of replication in a non-host cell type. In addition, we have packaged other RNAs, including RNA3 deletion mutants and RNA3-derived molecules which have the capsid protein sequence replaced with the bacterial chloramphenicol acetyltransferase gene sequence. This is a demonstration that viral/non-viral chimeric nucleic acid sequences can be packaged.

Particles which contain BMV-derived RNAs are formed in yeast as a result of BMV-dependent RNA replication of a wild-type RNA3. In yeast which express the viral replication proteins 1a and 2a (from plasmids pB1CT19 and pB2CT15, respectively) and replicate a wild-type RNA3 molecule expressed from pB3RQ39 or pB3MI10, particles are formed which again consist only of RNA and viral capsid protein. Particles derived from replication of an RNA3 expressed from pB3RQ39 sediment with an S value of approximately 67 in ½×VSB at 20° C. Gel electrophoresis shows two major bands which have been identified by Northern analysis as RNAs 3 and 4. This analysis also shows RNA which migrates more slowly than RNA3, and this material has been found by Northern analysis to include the messages for the 1a and 2a proteins. This is a physical demonstration of replication-derived selective packaging of viral-derived RNAs in a non-host cell type. Cryo-electron microscopy and digital image reconstruction generated images at 25 Å resolution. This technique reveals particles derived from replicative processes (wherein the RNA3 was derived from pB3MI10) with surface morphology and diameter (280 Å) indistinguishable from plant-derived particles.

General features of BMV-derived packaging in yeast. All of the classes of particles described above share several features. In all cases examined the yield of particles was sufficient to facilitate the physical characterization of the particles, at 5–50 µg per 500 ml culture. In all cases examined, approximately 20% of the total virus-derived or hybrid RNA in the yeast cell is recovered in free particles, while these RNAs are clearly a minor species in the cell. This is interpreted to be a useful efficiency of packaging of a desired nucleic acid. In all cases examined, the packaged BMV-derived sequences are visible as clear, sharp bands of the expected size on stained agarose gels of particle RNA. In contrast, specific cellular mRNA species are nearly undetectable by Northern analysis in the packaged RNA.

3. Discussion

The results reported here establish that *S. cerevisiae* can support robust FHV genomic replication and infectious virion synthesis. The results also show that an FHV-derived RNA replicon expressing a selected marker gene can be maintained persistently in yeast, conferring heritable phenotypic changes that should be useful in further genetic analysis of viral replication and gene expression.

De novo synthesis of FHV RNA and Drosophila-infectious virions in yeast. Following transfection of yeast spheroplasts with (+) strand FHV RNA1 and RNA2, all expected RNA products of FHV RNA replication and transcription appeared. The dramatic increase in (+) RNA1 and RNA2 between 0 and 84 hpt, as well as the appearance of (−) strand RNA1 and RNA2 replication intermediates and subgenomic RNA3, which were not present in the inoculuin, all demonstrated de novo RNA synthesis. As expected for RNA-dependent viral replication, accumulation of (−) strand RNA peaked first, followed in turn by (+) strand RNA, and then FHV PFU (FIG. 3). The sensitivity of these PFU to FHV-neutralizing antibodies, but not to ribonuclease, showed that they represented infectious virions. Moreover, particles resulted from packaging RNA synthesized in yeast, rather than from translation and repackaging of the inoculum: PFU accumulation increased exponentially between 12 and 48 hpt, (+) genomic RNA accumulation foreshadowed, temporarily and quantitatively, particle accumulation, and cell-associated inoculum at zero hpt was insufficient to account for the number of FHV particles.

Robustness of FHV RNA replication and particle synthesis in yeast. FHV replication in yeast mirrored that in Drosophila cells in multiple ways. First, the molar ratios of all FHV RNAs in yeast were similar to those in Drosophila cells. Second, the calculated yield of 2,000 PFU per infected spheroplast was comparable to the yield of 2,400 PFU per infected Drosophila cells (Schneemann, A., supra, 1992). This was initially surprising because yeast cells are normally much smaller than Drosophila cells. However, yeast spheroplasts are unable to regenerate their cell wall in liquid media (Necas, O., *Nature* (London) 192:580–581, 1961) and our microscopy showed that spheroplasts increased in size from 70 $\mu m^3$ (Sherman, F., in *Methods in Enzymology*, eds. Guthrie, C. and Fink, G. R. (Academic Press, Inc., San Diego, Calif.), Vol. 194, p. 17, 1991) at zerp hpt to about the size of a Drosophila cell, 360 $\mu m^3$, by 24 hpt, independently of infection. Finally, when the ratio of (+) strand RNA from FHV replication in BHK (baby hamster kidney) cells was analyzed by electrophoresis, (−) strand RNA2 sequences were found to migrate in at least two bands: a less prevalent band of monomeric RNA2, and a predominant band with mobility equivalent to dimeric RNA2 or double-stranded RNA2 (Ball, L. A., supra, 1994). Although both bands were observed, monomeric (−) RNA2 predominated in both insect and yeast cells under the conditions described here.

Expression and maintenance of heterologous markers in yeast by FHV RNA replication. Viral components required for FHV RNA replication were provided from FHV RNA1 cDNA plasmid p1R. RNA species comigrating with (+) and (−) RNA1 and RNA3 were present in total RNA extracted from cells containing p1R, but not from cells transfected with derivative with a frameshift in the FHV replication gene A.

When Ura$^-$ cells containing p1R were transfected with in vitro transcripts of DU, an FHV RNA2-derivative containing the URA3 gene, Ura$^+$ colonies were obtained. Three results indicated that the Ura$^+$ phenotype was dues to URA3 expression from DU, which was replicated as a free RNA and inherited by daughter cells. First, colony formation depended on FHV components in trans and cis. Second, PCR showed that the URA$^+$ phenotype was not a result of reverse-transcription of the RNA to DNA. TEhird, DU RNA and its (−) strand replication intermediate were found in Ura$^+$ prototrophs derived from DU-transfected spheroplasts many generations after transfection.

The ability of *S. cerevisiae* to support full FHV RNA replication and encapsidation, plus the ability of FHV to direct yeast phenotypes, means that the extensive resources of yeast can be used to analyze FHV. Among other opportunities, this provides powerful host genetics for identification and characterization of host factors required for FHV genomic replication, gene expression, and assembly.

We claim:

1. A method of synthesizing particles containing nucleic acid sequences comprising the steps of
  a) introducing a non-endogenous packageable nucleic acid sequence and a nucleic acid sequence encoding non-endogenous suitable capsid proteins into yeast cells, and
  b) inducing particle assembly, wherein at least one nucleic acid molecule is encapsidated within the particle, wherein the packageable nucleic acid sequence or the sequence encoding non-endogenous suitable capsid proteins comprises sequences from a member of the Nodaviridae or Bromoviridae family.

2. The method of claim 1, wherein the packageable nucleic acid sequence or the sequence encoding non-endogenous suitable capsid proteins comprises flock house virus or brome mosaic virus sequences.

3. A method of replicating a Nodaviridae virus nucleic acid sequence, comprising the steps of
  a) introducing a replicable nucleic acid sequence and a sequence encoding a suitable nucleic acid replication protein into yeast cells, wherein the replicable nucleic acid sequence or the sequence encoding a suitable nucleic acid replication protein comprises a Nodavirus sequence, and
  b) inducing viral nucleic acid replication.

4. The method of claim 3 wherein replicable nucleic acid sequence or the sequence encoding a suitable nucleic acid replication protein comprises flock house virus sequences.

5. The method of claim 3 wherein the yeast is of or associated with the family Saccharomycetaceae.

6. The method of claim 3 wherein the replicable nucleic acid sequence or the sequence encoding a suitable nucleic acid replication protein comprises a non-viral sequence.

7. The method of claim 6 wherein the non-viral sequence is a protein coding sequence.

8. The method of claim 7 additionally comprising the step of expressing the protein coding sequence.

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear     ( i i ) MOLECULE TYPE: Oligonucleotide     ( x i ) SEQUENCE DESCRIPTION: SEQ ID NO:1:

GCGGAGCTCT GTCGAAAGCT ACATATAAGG AA        32

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear     ( i i ) MOLECULE TYPE: Oligonucleotide     ( x i ) SEQUENCE DESCRIPTION: SEQ ID NO:2:

AGCGGCTTAA CTGTGCCCTC C        21

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear     ( i i ) MOLECULE TYPE: Oligonucleotide     ( x i ) SEQUENCE DESCRIPTION: SEQ ID NO:3:

TCGAGATCTT TAAAATG        17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear     ( i i ) MOLECULE TYPE: Oligonucleotide     ( x i ) SEQUENCE DESCRIPTION: SEQ ID NO:4:

TCGACATTTT AAAGATC                                          17